United States Patent [19]

Peeters et al.

[11] 4,319,024
[45] Mar. 9, 1982

[54] METHOD OF PREPARING β-ALKOXYACRLONITRILES

[75] Inventors: Hermann Peeters; Uwe Prange, both of Niederkassel; Wilhelm Vogt, Köln-Sülz, all of Fed. Rep. of Germany

[73] Assignee: Dynamit Nobel Aktiengesellschaft, Troisdorf, Fed. Rep. of Germany

[21] Appl. No.: 133,188

[22] Filed: Mar. 24, 1980

[30] Foreign Application Priority Data

Mar. 29, 1979 [DE] Fed. Rep. of Germany ....... 2912345
Mar. 29, 1979 [DE] Fed. Rep. of Germany ....... 2912344
Mar. 29, 1979 [DE] Fed. Rep. of Germany ....... 2912343
Aug. 1, 1979 [DE] Fed. Rep. of Germany ....... 2931228

[51] Int. Cl.$^3$ ................ C07C 121/30; C07C 121/48; C07C 121/75
[52] U.S. Cl. ................................ 542/413; 542/426; 544/163; 546/242; 546/246; 546/300; 546/330; 260/326.5 R; 260/464; 260/465 D; 260/465 E; 260/465 F; 260/465.6
[58] Field of Search ................ 260/465 F, 465.6, 464, 260/326.5 R; 542/413, 426; 544/163; 546/242, 246, 300, 330

[56] References Cited

U.S. PATENT DOCUMENTS

| | | | |
|---|---|---|---|
| 2,375,185 | 5/1945 | Bergel et al. ................ | 260/465.6 |
| 2,755,298 | 7/1956 | Whittaker ..................... | 260/465 F |
| 3,211,778 | 10/1965 | Kollonitsch .................... | 260/465.6 |
| 3,226,424 | 12/1965 | Jampolsky et al. ............. | 260/465.5 |
| 4,108,888 | 8/1978 | Rosen ............................. | 260/465 F |

Primary Examiner—Dolph H. Torrence
Attorney, Agent, or Firm—Sprung, Felfe, Horn, Lynch & Kramer

[57] ABSTRACT

A process for the preparation of a β-alkoxyacrylonitrile of the formula $$R'O—CH=CR—CN \qquad (C)$$

where R is hydrogen or an alkyl moiety, among others, by contacting a compound of the formula $$(1/aMe)\ O—CH=CR—CN \qquad (A)$$

where Me is an alkali metal or alkaline earth metal and α is 1 or 2 respectively, an elevated temperature with a halogen compound of the formula $$R'Hal \qquad (B)$$

where R' is among others a straight or branched alkyl or alkenyl moiety and Hal represents chlorine, bromine, or iodine. Also disclosed is a process for preparing a 3-amino-acrylonitrile of the formula

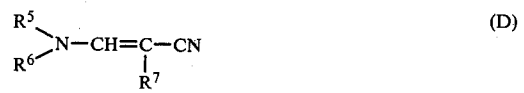

where $R^5$ and $R^6$ represent, among others, hydrogen, alkyl or alkenyl by contacting a 3-alkoxyacrylonitrile or a metal salt of 3-hydroxyacrylonitrile with ammonia and/or amine. Also disclosed is a process for the preparation of such 3-aminoacrylonitrile by contacting a 3-alkoxyacrylonitrile of the formula

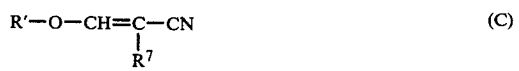

where R' has the meaning given above and $R^7$ has the same meaning as R stated above with an amine of the formula

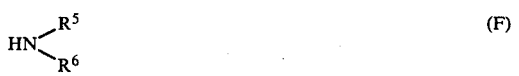

wherein $R^5$ and $R^6$ represent among others hydrogen, alkyl or alkenyl. The application further discloses a process for preparing a 3-amino-acrylonitrile of the formula

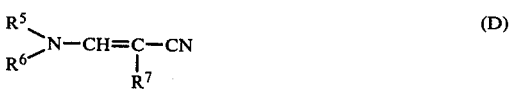

where $R^5$, $R^6$ and $R^7$ have the above meanings by contacting a compound of the formula

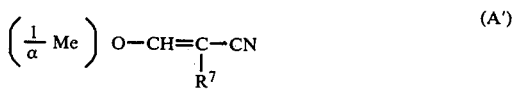

with an amine.

The Application also discloses the preparation of two-cyanovinyl esters by reaction of a cyanovinyl compound of the formula

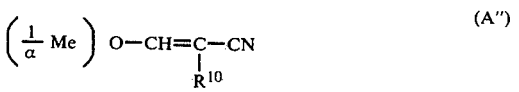

with an acid halide or an acid anhydride.

9 Claims, No Drawings

METHOD OF PREPARING β-ALKOXYACRLONITRILES

BACKGROUND

One aspect of the invention is the preparation of β-alkoxyacrylonitriles from metal salts of hydroxyacrylonitriles by transposition with halogen compounds.

The preparation of β-alkoxyacrylonitriles according to the state of the art is difficult.

A complicated synthesis of β-ethoxyacrylonitrile (I) by a plurality of steps has been described, which entails the tranposition of the sodium salt of β-hydroxyacrylic acid ethyl ester with ethanol in the presence of HCl to form β,β-diethoxypropionic acid ethyl ester, the preparation of the amide by reaction with ammonia, and further dehydration with phosphorus pentoxide, β-ethoxyacrylonitrile (I) being formed as a by-product (S. M. McElvain and R. L. Clark, J. Amer. Chem. Soc., 69, (1947) 2657).

In another, multiple-step synthesis, chloracetaldehyde is transposed with hydrocyanic acid to form α-hydroxy-β-chloropropionitrile, which then reacts with acetic anhydride to form α-acetoxy-β-chloropropionitrile. Pyrolysis of this compound leads to 33% β-chloroacrylonitrile. This reacts with alkali alcoholates to form β-alkoxyacrylonitrile (F. Scotti and E. J. Frazza, J. Org. Chem. 29, (1964) 1800).

β-Ethoxyacrylonitrile can be prepared by the transposition of isoxazole with sodium hydroxide to the sodium salt of β-hydroxyacrylonitrile and the alkylation of this compound in situ with diethyl sulfate or ethyl iodide (yield 37.6%). Isoxazole is obtained by the reaction of malonic dialdehyde acetal with hydroxylamine hydrochloride, so that the whole synthesis of β-ethoxyacrylonitrile is accomplished only from very expensive chemicals and requires a plurality of synthesis steps (GB Pat. No. 806,235).

The present invention, therefore, has the object of preparing β-alkoxyacrylonitriles in a simple manner and high yield by a method which is easy to practice on a technical and economical basis.

This object is accomplished in accordance with the invention by transposing an alkali or alkaline earth metal salt of β-hydroxyacrylonitriles of the General Formula A with alkyl halides of General Formula B in the presence of a stabilizer and catalyst system to form a β-alkoxyacrylonitrile of General Formula C.

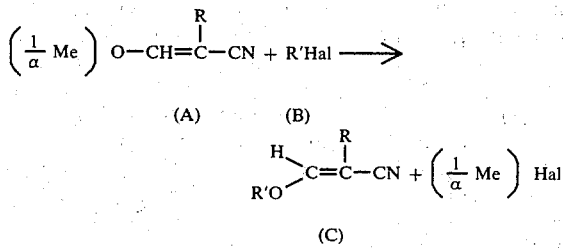

The subject matter of the invention is a method of preparing β-alkoxyacrylonitriles of the formula

R'O—CH=CR—CN (C)

wherein R represents H, straight-chain, branched or cyclic alkyl moieties of 1 to 20 carbon atoms, straight-chain or branched moieties —(CH$_2$)$_n$—CN, —(CH$_2$)$_n$—OR'' or —(CH$_2$)$_n$—CH(OR'')$_2$, wherein n=0 to 5 and R''=alkyl moieties of 1 to 12 carbon atoms, or —(CH$_2$)$_{n+1}$—Cyc, wherein Cyc represents isocyclic or heterocyclic mononuclear or polynuclear aromatic or cycloaliphatic ring systems having, in some cases, substituents on the rings, especially those of 5–8 carbocyclic carbon atoms per ring and n=0 to 5, and wherein R' represents straight-chain or branched alkyl or alkenyl moieties of 1 to 12 carbon atoms, isocyclic or heterocyclic mononuclear or polynuclear aromatic or cycloaliphatic ring systems, bearing substituents in some cases, especially those of 5–8 carbocyclic carbon atoms per ring, or —(CH$_2$)$_p$—Cyc wherein Cyc has the same meaning as above, the moieties —(CH$_2$)$_p$—OR''' or —(CH$_1$—CH$_2$—O)$_q$—R''' with p=1 to 5 and q=1 to 4 and R'''=straight-chain or branched alkyl moieties of 1 to 12 carbon atoms, which is characterized by contacting, at elevated temperature, a compound of the formula (1/αMe)O—CH=CR—CN (A)

wherein R has the same meaning as above and Me is an alkali metal when α=1 or an alkaline earth metal when α=2, with a halogen compound of the formula R'—Hal(B), wherein R' has the meaning given above and Hal represents chlorine, bromine or iodine, in the presence of a basically reacting compound of the alkali or alkaline earth metals, as stabilizer.

The substituents R and R' are generally those which are inert with respect to the reactants. In the substituents R and R', those alkyl or alkenyl moieties which have 1 to 6 carbon atoms are preferred. Of the moieties containing cyclic ring systems, those which are mononuclear, i.e., monocyclic, are greatly preferred, and of those which are polynuclear the bicyclic are preferred.

In the polynuclear ring systems, the rings can be joined together directly by one or more atoms or they can be joined by means of one or more carbon atoms or heteo atoms as bridges.

The cycloaliphatic ring systems are preferentially cycloalkane moieties, but they may also contain one or more double bonds.

The heterocyclic moieties contain preferentially nitrogen, and in some cases also oxygen or other hetero atoms.

If there are to be substituents in the ring systems, they can be any substituents desired, provided they may be inert in the reaction. Preferred are lower alkyl groups of 1 to 3 carbon atoms, chlorine, or methoxy, ethoxy or carbalkoxy groups. Particularly contemplated mono and polycyclic rings are those derived from the following cyclic compounds phenyl, benzyl, naphthyl, disphenyl anilino, pyridyl, lower 1 to 3 alkyl pyridyl morpholino, piperidyl, lower 1 to 3 alkyl piperidyl and pyrrolidino.

The alkali or alkaline earth salts of β-hydroxyacrylonitriles of General Formula A, which are used in preparing the β-alkoxyacrylonitriles, can be prepared from alkyl cyanides, formic acid esters and alkali or alkaline earth alcoholates according to the principle of the Claisen ester condensation. A better method of preparing compounds of General Formula A, however, is described in German Patent Application No. P 27 53 322.8 and U.S. Application Ser. No. 963,713 filed Nov. 27, 1978, assigned to the assignee herewith, the disclosure which is hereby specifically incorporated herein by reference, in which alkyl cyanides are transposed with alkali or alkaline earth alcoholates in the presence of carbon monoxide. One can use the compounds of General Formula A prepared pursuant to this patent application directly, without further processing.

Sodium or potassium salts are preferred as alkali or alkaline earth compounds of Formula A on account of their easy accessibility. One can, however, use rubidium, cesium, magnesium or calcium salts.

The chlorine compounds are preferred as halogen compounds of Formula B, particularly methyl chloride, ethyl chloride, propyl chloride, isopropyl chloride, n-butyl chloride, isobutyl chloride, sec. butyl chloride, tert. butyl chloride, 2-methoxyethyl chloride, cyclohexyl chloride, allyl chloride, or benzyl chloride. The corresponding bromides or iodides can also be used, but they offer no advantage over the economically more attractive chlorides.

The halogen compounds are used in stoichiometric amounts or in an excess, preferably in a ratio of 1 to 2 moles of halogen compound per mole of compound of General Formula A. The excess halogen compound can be recycled.

A basically reacting compound of the alkali metals or alkaline earth metals is added to the reaction mixture as a stabilizing component, examples being alkali metal hydroxides, alkali hydrogen carbonates or alkali carbonates, as well as alkaline earth oxides, alkaline earth hydrogen carbonates or alkaline earth carbonates, such as NaOH, KOH, NaHCO$_3$, KHCO$_3$, Na$_2$CO$_3$, K$_2$CO$_3$, MgO, CaO, MgCO$_3$ and CaCO$_3$. CaO is used with preference.

The basically reacting compound is used in a ratio of 0.05 to 1 equivalent per mole of compound of General Formula A.

It is greatly preferred to use catalysts which increase the selectivity and speed of the reaction, consisting preferentially of quaternary ammonium salts of the formula:

wherein $R^1$, $R^2$, $R^3$ and $R^4$ represent identical or, in some cases, different, linear or branched cycloalkyl, aryl, alkaryl, aralkyl or alkyl moieties of 1 to 20 carbon atoms, and X represents an univalent anion of an acid.

Of the cyclic moieties, monocyclic moieties are preferred, and of the aliphatic moieties those having 1 to 6 carbon atoms are preferred.

Examples of $R^1$ to $R^4$ are methyl, ethyl, propyl, butyl, octyl, cetyl, benzyl or phenyl. Examples of anions are fluoride, chloride, bromide, iodide, hydrogen sulfate, hexafluorophosphate, cyanide, azide, nitrate, nitrite, perchlorate, tetrafluoroborate, cyanate, thiocyanate, trifluoromethanesulfonate, 4-toluenesulfonate and hexafluoroarsenate. A preferred compound is tetra-n-butylammonium chloride, bromide or iodide.

The crown ethers that can be used instead of the quaternary ammonium salts are cyclic ethers of glycols in which the numbers indicate the number of glycol groups. They are, for example, 15-crown-5, 18-crown-6, dibenzo-18-crown-6 and dicyclohexyl-18-crown-6*
*(see F. Vögtle and E. Weber: "Kontakte" 1977, 1 p. 11; 1977, 2, p. 16; 1977, 3 p. 36 published by Merck Comp. Germany)

The quaternary ammonium salt of General Formula D or of the crown ethers are used in catalytic amounts with respect to Compound A. In general, 10$^{-3}$ to 10$^{-1}$ moles of quaternary ammonium salt or crown ether are used per mole of compound A. Higher concentrations are possible, but economically undesirable.

An iodine compound can be added to the catalyst. One can use, therefor, a substance consisting of an iodide or a compound giving off iodine ions under the reaction conditions. By this means the highest reaction rates and best yields are generally achieved. For example, the quaternary ammonium salt of General Formula O can be added in the form of an iodide. It is furthermore possible to add to the alkyl halide of General Formula B small amounts of the corresponding iodide. An inorganic salt with an iodide anion can be added. For example, LiI, NaI, KI, CuI, ZnI$_2$ or CoI$_2$ can be used. The iodine compound is added in a ratio of 10$^{-3}$ to 10$^{-1}$ moles per mole of compound of General Formula A.

Aprotic solvents are appropriate. For example, alkanes, benzene or toluene are solvents of the hydrocarbon series which can be used. Ethers can be used, such as tetrahydrofuran, dimethoxyethane, and di-, tri- or tetraglymes. Polar aprotic solvents, such as hexamethylphosphoric acid triamide, dimethylsulfoxide, dimethylformamide or acetonitrile are also good solvents for the reaction. The process can be operated with or without the use of solvents.

The solvents can be used in quantities of 0.5 to 2 liters per mole of the compound of General Formula A. Larger amounts of solvent are possible, but offer no advantage.

A temperature range of 60° to 220° C. has proven to be a desirable one for the reaction. Particularly when chlorine compounds are used as the halogen compounds of Formula B, it is advantageous to keep the reaction temperature in the range from 80° to 180° C., in order to achieve sufficiently rapid reactions. The reaction time is between 1 and 8 hours, depending on the reaction temperature, during which a complete transformation of Compound A is achieved.

The reaction can be preferred at standard pressure, at reduced pressure or at excess pressure up to 50 atmospheres. Higher pressures are possible but not desirable. Preferably the pressure is between standard (atmosphere) pressure and the self pressure of the reactants.

The reaction can be performed as follows: The starting substance A, together with the basically reacting inorganic salt, the quaternary ammonium salt, and the iodine compound if used, dissolved or suspended in the solvent, is placed under inert gas in a reactor provided with a stirrer. Then starting substance B is added, and the reactor is closed and raised under the self-pressure to the reaction temperature. After the reaction has ended, the reactor is cooled and vented, and the reaction mixture is taken out. The solid is separated by filtration or centrifugation, and the end substance C is isolated, for example by fractional distillation.

β-Alkoxyacrylonitriles are valuable starting substances for the preparation of heterocyclic compounds. For example β-alkoxyacrylonitriles of the Formula

can be reacted with urea to form cytosine derivatives substituted in 5-position (G.B. Pat. No. 806 235):

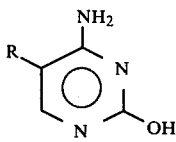

Cytosin and its derivatives can be used as anti-tumor drugs (Belgian Pat. No. 74 74 76) agrochemicals (Japanese published Application No. 65-68 113) or as photochemicals (German Pat. No. 25 06 320).

GENERAL DESCRIPTION OF THE EXPERIMENTS

An alkali or alkaline earth salt of a β-hydroxyacrylonitrile, a basically reacting salt, a quaternary ammonium salt of General Formula D, and an iodine compound are placed in an aprotic solvent under a nitrogen gas atmosphere in a reactor equipped with a stirrer. Depending on the state of the alkyl halide of General Formula B, the latter is also added or condensed in. The reactor is closed, and is heated to the reaction temperature at its self-pressure. At the end of the reaction the reactor is cooled and, in the case of alkyl halides B which are gaseous under saturated conditions, the reactor is vented. The reaction mixture is freed of solid components by a filter or centrifuge, and is then fractionally distilled. Depending on the boiling point of the solvent, first the solvent or first the reaction product is obtained. The solvent can be used again for the reaction.

The reaction product consists of a mixture of e and z isomers. If compounds of General Formula A are used in which R=H, the reaction mixture contains the α-alkyl-substituted compound, hereafter C, in addition to the δ-alkoxyacrylonitrile C. In order to achieve a better distillative separation of the main products from this by-product, it is advantageous to treat the reaction solution with mineral acids such as $H_2SO_4$, $H_3PO_5$ or HCl, causing the z-configured isomer to be transformed to the more stable e-isomer. In this manner, greater boiling point differences are created between the main product C and the α-alkyl-substituted by-product (C').

Another aspect of the invention is the preparation of 3-aminoacrylonitriles from β-alkoxyacrylonitriles by transposition with amines.

In the state of the art, 3-aminoacrylonitriles of Formula I are hardly accessible or only on the basis of expensive starting products, e.g., by the transposition of 3-chloroacrylonitrile with various amines (J. org. Chem. 29, (1964), 1800), dehydrogenation of 3-dimethylaminopropionitrile or condensation of acetonitrile with dimethyl formamide acetal to 3-dimethylaminoacrylonitrile (U.S. Pat. No. 3,966,791), addition of amines onto cyanoacetylene (J. chem. Soc. [London] C 1969, 1086), reduction of malodinitrile with $LiAlH_4$ to 3-aminoacrylonitrile (Angew. Chemie 81, (1969) 432), or alkaline cleavage with pyrazoles (C.A. 64, (1966) 3516 h).

The subject matter of the invention is a method of preparing 3-aminoacrylonitriles of Formula E:

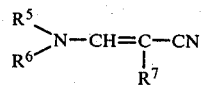

wherein $R^5$ and $R^6$ represent hydrogen, identical or different straight-chain or branched alkyl, alkenyl or alkynyl moieties of 1 to 12 carbon atoms, —Cyc—$(CH_2)_n$—Cyc, wherein Cyc represents isocyclic or heterocyclic, mononuclear or polynuclear, aromatic or cycloaliphatic ring systems which can in some cases have substituents on the rings, especially those having 5 to 8 carbocyclic carbon atoms per ring, and n=0 to 5, the grouping —X—$R^8$, wherein X represents straight-chain, branched or cyclic alkene or alkenyl moieties having 2 to 12 carbon atoms, —Cyc—, —$(CH_2)_n$—Cyc or —$(CH_2)_n$Cyc—$(CH_2)_n$— wherein Cyc and n have the above meaning and

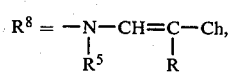

or $R^5$ and $R^6$ together form alkylene or alkenylene moieties of a ring of 3 to 6 members, which in some cases is interrupted by one or more hetero atoms, and $R^7$ has the same meaning as R in Formula C, characterized in that a 3-alkoxy-acrylonitrile of the formula

 (C)

wherein R' has the meaning stated above is reacted with an amine of the formula

 (F)

wherein $R^5$ and $R^6$ have the meaning given above, and R' and $R^7$ have the same meaning as R' and R in Formula C. respectively.

The nature of the substituents $R^5$, $R^6$ and $R^7$ must be governed according to the substituents required in the end product, especially when the products of the process are used as intermediates for other syntheses. In general, the substituents should be inert with respect to the reactants.

In the polynuclear ring systems, the rings can be joined together directly by one or more atoms, or they can be joined by one or more carbon atoms or hetero atoms as bridges.

The cycloaliphatic ring systems are preferentially cycloalkane moieties, but they can also contain one or more double bonds.

The heterocyclic moieties contain preferably nitrogen, and in some cases also oxygen or other hetero atoms such as sulfur and phosphorus. The substituents, if any, of the ring systems can be any desired substituents, provided they be inert in the reaction. Low alkyl groups of 1 to 3 carbon atoms, chlorine, and in some cases alkoxy moieties, are preferred. The radicals R, (or $R^7$) to the extent that they represent alkyl or alkenyl moieties, are preferably short-chain moieties of 1 to 6 carbon atoms. Of the moieties R (or $R^7$) containing cyclic ring systems, mononuclear moieties, i.e., monocyclic moieties, are greatly preferred, and of the polynuclear moieties the bicyclic are preferred.

Preferred moieties $R^5$ and $R^6$ are hydrogen, low aliphatic moieties of 1 to 6 carbon atoms, mononuclear aromatic or cycloaromatic moieties, such as those of aniline or pyridine, and if $R^5$ and $R^6$ together form rings, the rings of morpholine, piperidine and pyrrolidine are preferred. In the case of the reaction products of diamines with the grouping $R^5$—X—$R^8$, $R^8$ is preferably hydrogen.

The easily accessible low alkyl moieties of 1 to 6 carbon atoms are especially preferred as moieties $R^5$, and of these, methyl to propyl moieties are especially preferred.

The process of the invention is best performed by contacting a 3-alkoxyacrylonitrile and an amine, without solvent, in an inert polar organic solvent such as an alcohol, in acetonitrile, in a polar aprotic solvent such as dimethylformamide or dimethylsulfoxide, etc., in a nonpolar organic solvent such as benzene, ether, n- or cyclo-paraffin, in water or in suitable mixtures thereof. The amount of the solvent that is used is not critical, but excessive dilution prolongs the reaction time.

The reaction can be performed at temperatures ranging from −30 to about 250° C., preferably from +10° C. to the boiling point of the reactants. In some cases high yields are obtained in a short period even at low temperatures. The reaction time depends on the temperature and generally amounts to about one-half to 5 hours.

The reaction can be performed at standard (atmospheric) pressure, at reduced pressure or at excess pressure up to 50 bars. Higher pressures are possible, but not desirable. Preferably the pressure is between standard pressure and the self-pressure of the reactants. Autogeneous pressure is contemplated especially when a closed reaction vessel is used.

The reaction can be performed, if desired, with distillation of the alcohol R'OH that forms in the course of the reaction, but the only advantage is that, when operating at standard pressure, for example, the reaction temperature can be increased if desired.

The ratio of the molar equivalents of amine (F) to 3-acrylonitrile (C) can be greater than, smaller than, or equal to 1, depending on whether a substantially complete transposition of amine (F) or 3-alkoxyacrylonitrile (C) is to be achieved. In general, a ratio of 4:1 to 1:4 is maintained, although great excesses of one reactant, up to 1:10, may be desirable.

The reaction products can be separated simply by distillation, crystallization or extraction with a suitable solvent. They are obtained in a high yield and great purity.

The reaction products are usually a mixture of cis and trans isomers, the trans isomers generally being preponderant.

If amines are to be transposed which react less easily or incompletely with 3-alkoxyacrylonitriles of formula C for example the less basic aromatic amines, a second reactive amine can be added, which catalyzes the reaction and does not occur in the end product. Ammonia is an example of these reactive amines, although other amines are also usable, such as morpholine or picoline.

The amount of the reactive amine can be one equivalent, or more or less than one equivalent.

One can also perform the reaction first with a reactive amine, and also, if desired, to isolate the product, and then to prepare the desired amino-acrylonitrile with one of the less easily reacting amines.

3-Aminoacrylonitriles of Formula E can be used for the preparation of a variety of heterocyclic compounds, such as for example cytosine, pyrimidines, isoxazoles, 5-aminopyrazoles, malonic acid dinitrile, aminomethylenemalonic acid nitriles, herbicides, or as a comonomer for the preparation of polymer plastics.

More closely 3-aminoacrylonitriles of the Formula

$$R^5R^6N—CH=C—CN \atop R_7 \qquad (E)$$

can be reacted with arylhydrazines of the Formula

$$R^{11}—NH—NH_2$$

to 1-aryl-5-aminopyrazoles of the Formula

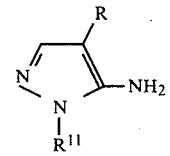

which are usable in known manner as coupling agents for azo coloring matter (see Deutsche Offenlegungsschrift No. 1 940 686) and intermediates for the production of sulfonamides according to the Belgian Pat. No. 557 254.

Another aspect of the invention is the preparation of 3-aminoacrylonitriles from metal salts of hydroxyacrylonitriles by transposition with amines.

The present invention relates to a method of preparing 3-aminoacrylonitriles of the formula

$$\begin{matrix} R^5 \\ R^6 \end{matrix} \!\!\!\!\! >\!\! N—CH=C—CN \atop R^7 \qquad (E)$$

wherein $R^5$, $R^6$ and $R^7$ have the same meaning as already given for substances of Formula E, which is characterized by contacting a compound of the formula

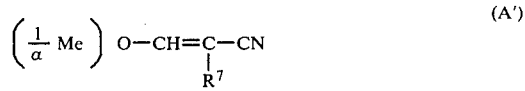

$$\left(\frac{1}{a}\,Me\right)\,O—CH=C—CN \atop R^7 \qquad (A')$$

wherein $R^7$ has the meaning given above and Me is an alkali metal with $a=1$ or an alkaline earth metal with $a=2$, with an amine of the formula

$$\begin{matrix} R^5 \\ R^6 \end{matrix} \!\!\!\!\! >\!\! N—H \qquad (F)$$

wherein $R^5$ and $R^6$ have the meaning given for substances of Formula D, in the presence of a monobasic or polybasic inorganic or organic acid or in the presence of a salt of an inert amine, or with an amine salt of one of the named acids and an amine of Formula F.

The process of the invention can be performed by adding the metal salts of 3-hydroxyacrylonitriles of Formula A, in the form of a solid, suspension or solute, to the suspension or solution of the amine of Formula F and the monobasic or polybasic inorganic or organic acid, or to the suspension or solution of the amine salt, or to the suspension or solution of the amine of Formula E and of a salt of an inert amine. The substance of Formula A and the amine of Formula E can be placed in the reactor in solution or suspension, and then the acid can be added, or the substances of Formula A can be placed in the reactor and the amine salt can be added. The inert amines added are tertiary amines which do not participate in the reaction on account of the lack of hydrogen atoms.

The starting substances are easily accessible in accordance with German Patent Application No. P 27 53 322.8 and U.S. Ser. No. 963,713, supra.

The amine salt that is to be formed from the amine of Formula F and the acid can be prepared "in situ" in the reaction solution of the corresponding amine and the acid, by reacting in the ratio of their molar equivalents, or it can be put in as an isolated salt. Suitable acids are, for example, hydrochloric acid, sulfuric acid, phosphoric acid, and acetic acid, although other common acids can also be used. Amine salts are preferably the hydrochlorides or sulfates. The ratio of the molar equivalents of the amines or amine salts to the substance of Formula A should be from 1:1 to 6:1, and advantageously from 1:1 to 3:1. The amount of the acid or salt of an inert amine can be equivalent to the amine of Formula F, but an excess of acid can also be used. The reaction can take place in an inert polar or nonpolar, neutral, basic or acid organic solvent, in water, or in suitable mixtures thereof. The reaction can also be conducted in the absence of a solvent.

Examples of suitable solvents are: alcohols of 1 to 6 carbon atoms, acetonitrile, dimethylformamide, dimethylsulfoxide, amines, e.g., an excess of the amine that is reacted, or an inert tertiary amine, acetic acid, benzene, toluene, or ether, although this selection is not to be considered restrictive.

The amount of the solvent should be enough to enable the reaction mixture to be stirred easily. There is no maximum limit, although excessive dilution results in lower yields and a lengthening of the reaction time.

In the reaction of weakly basic amines, such as the aromatic or heteroaromatic amines, water is to be avoided as solvent or as component of the solvent. All of the reactants are, therefore, to be used in dry form, substantially free of water.

The reaction can be performed in the temperature range from $-10°$ C. to $200°$ C. or more, preferably from $0°$ C. to the boiling point of the solvent. The reaction time is dependent upon the applied reaction temperature and is between about 1 hour and 48 hours. The pressure is to be generally between standard pressure and 50 bars. Higher pressures are possible, but of no benefit. Preferentially, the reaction is performed between standard pressure and the self-pressure of the reactants. In the latter case a closed reaction vessel is used.

After any unreacted salt or salt formed in the reaction has been removed by distillation, the reaction mixture is processed cold by concentrating the mother liquor and then distilling or crystallizing, or by extraction with a suitable solvent from the aqueous reaction solution.

The reaction products are generally produced in the form of a mixture of cis and trans isomers, the trans isomers usually predominating.

The products are conclusively identified by infrared spectroscopy, NMR spectroscopy and mass spectroscopy.

The final aspect of the invention is the preparation of 2-cyano vinyl esters from metal salts of hydroxyacrylonitriles by reaction with acid halides or acid anhydrides.

The present invention relates to a process for the preparation of 2-cyanovinyl esters of the general formula:

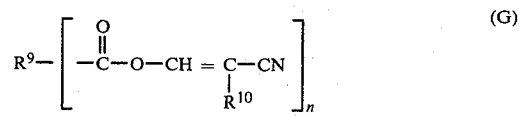
(G)

wherein n is 1 or 2 and $R^9$ represents straight-chain or branched alkyl, alkylene, alkenyl or alkenylene moieties of 1 to 12 carbon atoms, isocyclic or heterocyclic ring systems having a mono- or polycyclic structure, especially one having 5 to 7 carbocyclic carbon atoms per ring, or $(CH_2)_m$—Cyc, wherein —Cyc represents an isocyclic or heterocyclic ring of a mono- or polycyclic structure, which can have substituents on the ring, and m represents 0 to 5, and R has the same meaning as in Formula A, which process is characterized by the fact that a compound of the formula

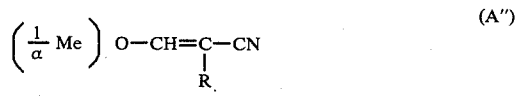
(A″)

in which R has the same meaning as in Formula A and Me is an alkali metal with $\alpha=1$ or an alkaline earth metal with $\alpha=2$, is contacted with an acid halide of the formula:

(H)

wherein n and $R^9$ have the same meaning as in Formula G, and Hal represents chlorine or bromine, or with an acid anhydride of the formula:

(I)

wherein $R^9$ has the same meaning as in Formula (G).

On the basis of U.S. Pat. No. 3,288,799, it is known to prepare 2-cyanovinyl esters of organic carboxylic acid by contacting 3-chloroacrylonitrile with a carboxylic acid. On account of the difficulty of preparing 3-chloroacrylonitrile, this process is commercially unsatisfactory.

The present process offers a considerable advantage over the known processes, since the reaction is performed easily with high yields and the starting products, in the form of the acid chlorides (G) or acid anhydrides (H), as well as the 2-cyanovinyl alcoholates, are easy to obtain in accordance with German Pat. No. P 27 53 322.8 and U.S. Application Ser. No. 963,713.

It is desirable to perform the process of the invention by adding the acid halide of Formula G or the acid anhydride of Formula H, dissolved or suspended in an inert polar or non-polar solvent, if desired, to the suspension of the cyanovinyl alcoholate of Formula A in the polar or non-polar solvent. While this is being done, cooling to −40° or to 20° C. is advantageous. The reaction that follows is performed at temperatures of −40° to 100° C., preferably −10° to 50° C.

Examples of suitable inert solvents are benzene, toluene, ether, tetrahydrofuran, n- or cyclo-paraffins, acetone, acetonitrile, dimethylformamide or dimethylsulfoxide. The solvents must be anhydrous. The amount of the solvent must be at least sufficient to enable the reaction mixture to be stirred, and there is no maximum, except that excessive dilution reduces the yield and lengthens the reaction time. The reaction time is dependent upon the reaction temperature and the nature of the reactants, and amounts in general to from one to 24 hours.

The starting substances can be in equivalent amounts or there can be an excess of one component, it being desirable to use an excess of the more easily available component, i.e., the acid halide or the acid anhydride, as the case may be.

The molar ratio of acid halide of Formula H or acid anhydride of Formula I to the cyanovinyl alcoholate of Formula A is to be generally 1:1 to 4:1, and preferably 1:1 to 2:1, when $n=1$, and, when $n=2$, it is to be from 0.5:1 to 2:1, preferably 0.5:1 to 1:1.

The reaction mixture is worked up after the reaction simply by filtering out the salt Me $Hal_n$ that has formed, plus any unreacted cyanovinyl alcoholate, and then distilling off the solvent and excess reagent, followed by distillation or crystallization.

The 2-cyanovinyl esters of Formula F may be used as starting materials for the preparation of cyanoethyl carboxylates. This involves hydrogenating the olefinic unsaturation present in the cyanovinyl esterifying group. A method by which this can be accomplished is hydrogenation with palladium-on-char-coal catalyst in a Par apparatus until the theoretical quantity of hydrogen has been absorbed.

Additionally, those compounds which contain an azo, anthraquinone, thiazole, oxazole, pyrazole, xanthene, triarylmethane, phthalocyanine or other colored residue, may be employed as the coloring component in dyestuff and pigment compositions. Thus esters of Formula 1 containing an azo moiety may be dyed on cellulosic esters, polyesters and polyamides, using standard dyeing procedures.

It is to be understood that the substituents $R^8$ and R of the substances produced in accordance with the invention are quite different, according to the constitution which the cyanovinyl esters serving as intermediates are to have and which the end products made with them are to have for their intended application. Accordingly, the substituents $R^8$ and R can be of simple construction, as well as specially constructed with a very specific structure and having very specific functional groups.

Aside from that, in a number of cases those substituents $R^9$ and R are preferred which correspond to the aliphatic monocarboxylic acids of 1 to 6 carbon atoms atoms, especially the alkanoic acids, the aliphatic dicarboxylic acids of 1 to 6 carbon atoms, especially the alkanoic diacids, the unsubstituted aromatic mono- and dicarboxylic acids as well as their simple substitution products containing, for example, methyl or chloro substituents. Particularly contemplated are the substitute mono and di-alkanoic acids.

With regard to the substituents R, aliphatic substituents having 1 to 8 carbon atoms or substituted or unsubstituted benzyl moieties are also preferred in many instances.

EXAMPLES

The following examples will serve for the further explanation of the invention.

The products were identified by infrared spectroscopy, nuclear magnetic resonance and mass spectroscopy.

EXAMPLES 1 TO 9

In this series of experiments, a variety of alkylating agents R′-Hal were used.

In each case, 0.5 mol of $NaOCH=CH-CN$, 500 ml of acetonitrile, 1 g of sodium iodide, 5 g of tetra-n-butylammonium bromide and 0.5 mol of calcium oxide were used.

| Example No. | R′—Hal | Reaction time (h) | Temp. °C. | Yield % C | % D |
|---|---|---|---|---|---|
| 1 | $CH_3Cl$ | 1.5 | 130 | 60 | 15 |
| 2 | $C_2H_5Cl$ | 6 | 130 | 82 | 10 |
| 3 | $n-C_3H_7Br$ | 2.5 | 80 | 75.5 | 12 |
| 4 | $iso-C_3H_7Cl$ | 4 | 175 | 88.9 | 5.2 |
| 5 | $iso-C_3H_7Br$ | 3.5 | 80 | 84.6 | 6 |
| 6 | $sec.-C_4H_9Cl$ | 6 | 150 | 63.04 | 4.5 |
| 7 | benzyl chloride | 4 | 80 | 50.0 | |
| 8 | allyl chloride | 6 | 80 | 55 | * |
| 9 | allyl bromide | 4 | 80 | 60 | * |

*not determined

EXAMPLES 10 TO 13

In this series of experiments different starting substances A were used.

In each case, 0.5 mole of compound A, 1 mole of ethyl chloride, 500 ml of acetonitrile, 1 g of sodium iodide, 5 g of tetra-n-butylammonium bromide and 0.5 mole of calcium oxide were used.

| Example No. | Compound A | Reaction Time (h) | Temp. °C. | Yield % C | % D |
|---|---|---|---|---|---|
| 2 | $NaO-CH=CH-CN$ | 6 | 130 | 82 | 10 |
| 10 | $KOCH=CH-CN$ | 2 | 150 | 84 | 6.5 |
| 11 | $NaOCH=C(CH_3)-CN$ | 2 | 160 | 82 | — |
| 12 | $NaOCH=C(C_2H_5)-CN$ | 2 | 160 | 80 | — |
| 13 | $NaOCH=C(CH_2-C_6H_5)-CN$ | 6 | 150 | 89.2 | — |

EXAMPLES 14 TO 19

In this series of experiments different aprotic solvents were used.

In each case, 0.5 mol of A, 1 mol of $C_2H_5Cl$, 500 ml of solvent, 1 g of sodium iodide, 5 g of tetra-n-butylammonium bromide and 0.5 mol of calcium oxide were used, and compound A was $NaOCH=CH-CN$.

| Example No. | Solvent | Reaction time (h) | Temp. °C. | Yield % C | % D |
|---|---|---|---|---|---|
| 14 | Acetonitrile | 2 | 160 | 83 | 12 |
| 15 | Acetone* | 2 | 120 | 78 | 10 |
| 16 | Benzene | 4 | 160 | 84 | 12 |
| 17 | Acetic acid ethyl ester | 2 | 130 | 73 | 10 |
| 18 | 1.2-dimethoxyethane | 2 | 130 | 60 | 11.6 |
| 19 | Dimethylformamide | 2 | 130 | 80 | 11.4 |

*Additional formation of diacetone alcohol

EXAMPLES 20 TO 22

In this series of experiments, different iodide promoters were tested.

In each case, 0.5 mol of NaO—CH=CH—CN, 1 mol of $C_2H_5$—Cl, 500 ml of acetonitrile, 1 g of iodide promoter, 5 g of tetra-n-butylammonium bromide and 0.5 mol of calcium oxide were used.

| Example No. | Iodide promoter | Reaction time (h) | Temp. °C. | Yield % C | % D |
|---|---|---|---|---|---|
| 14 | NaI | 2 | 160 | 83 | 12 |
| 20 | KI | 2 | 160 | 82 | 12 |
| 21 | $ZnI_2$ | 2 | 160 | 80 | 11 |
| 22 | $C_2H_5I$ | 2 | 150 | 82 | 14 |

EXAMPLES 23 TO 26

In this series of experiments, different basic compounds were used as stabilizers.

In each case, 0.5 mol of NaOCH=CH—CN, 1 mol of $C_2H_5Cl$, 500 ml of solvent, 1 g of sodium iodide, 5 g of tetra-n-butylammonium bromide and 0.5 mol of basic compound were used. The reaction time was 2 hours at 160° C.

| Example No. | Basic Component | Solvent | Yield % C | % D |
|---|---|---|---|---|
| 14 | CoO | Acetonitrile | 83 | 12 |
| 23 | MgO | Benzene | 68 | 14 |
| 24 | NaOH | Benzene | 60 | 20 |
| 25 | $NaOOCCH_3$ | Acetonitrile | 49 | 10 |
| 26 | $K_2CO_3$ | Acetonitrile | 62 | 11 |

EXAMPLES 27 TO 30

In this series of experiments, different ammonium salts D or crown ethers were used.

In each case, 0.5 mol of NaOCH=CH—CN, 1 mol of $C_2H_5CL$, 500 ml of acetonitrile, 1 g of sodium iodide and 0.5 mol of calcium oxide were used. The reaction time was 2 hours at 160° C.

| Example No. | D or crown ether | Quant. g | Yield % C | % D |
|---|---|---|---|---|
| 14 | tetra-n-butylammonium bromide | 5 | 83 | 12 |
| 27 | tetra-n-butylammonium bromide | 2.5 | 82 | 11 |
| 28 | tetra-n-butylammonium chloride | 3 | 82 | 12 |
| 29 | Dibenzo-18-crown-6 | 5 | 59 | 13 |
| 30 | 18-crown-6 | 2.5 | 69.4 | 15.2 |

Examples of the Preparation of 3-Amino-acrylonitriles

The substances prepared were identified by NMR spectroscopy, infrared spectroscopy and mass spectrometry.

EXAMPLE 31

19.4 g (0.2 mol) of 3-ethoxyacrylonitrile (3-EAN) and 25.5 g (1.5 mol) of ammonia are heated at 100° C. for 4 h in an autoclave. After venting off the ammonia and distilling the ethanol, 11.0 g (81%) of 3-aminoacrylonitrile was obtained.

$^1$H-NMR ($CDCl_3$): $\delta$=3.96 (d, $I_{cis}$=9.2 Hz, CH—CN), 4.25 (d, $I_{tr}$=14 Hz, CH—CN), 4.8–6.4 (broad, NH), 6.4–7.9 (m, CH—N).

EXAMPLE 32

19.4 g (0.2 mol) of 3-EAN and 38 g of 40% aqueous solution of methyl amine (0.5 mol) are stirred for 3 h at 25° C. After extraction with ether, drying and vacuum distillation, 15.4 g (93.8% with respect to the 3-EAN) of 3-methylaminoacrylonitrile was obtained.

$^1$H-NMR ($CDCl_3$): 2.68 Cd, $I_{NH}$=5.0 Hz, $CH_{3tr}$, 2.8), 2.98 (d, $I_{NH}$=5.0 Hz, $CH_{3\,cis}$, 0.2), 3.67 (d, $I_{cis}$=8.5 Hz, CH—CN), 3.83 (d, $I_{tr}$=13.5 Hz, CH—CN), 5.71 (broad, NH, 1), 6.60 (dd, $I_{NH}$=12.0 Hz, $I_{cis}$=8.5 Hz, CH—N), 712 (dd, $I_{NH}$=7.1 Hz, $I_{tr}$=13.5 Hz, CH—N).

EXAMPLE 33

48.5 g (0.5 mol) of 3-EAN and 90 g (2 mol) of dimethylamine in 150 ml of benzene are kept at 55° C. for 3 h. Subsequent distillation in vacuo yields 46.1 g (96.1% with respect to 3-EAN) of 3-dimethylaminoacrylonitrile.

$^1$H-NMR ($CCl_4$): $\delta$=2.92 (s, $CH_{3tr}$=5.4), 317 (s, $CH_{3cis}$, 0.6) 3.57 (d, $I_{cis}$=9.5 Hz, CH—CN, 0.1), 3.75 (d, $I_{tr}$=13.5 Hz, CH—CN, 0.9), 6.50 (d, $I_{cis}$=9.5 Hz, CH—N, 0.1), 7.15 (d, $I_{tr}$=13.5 Hz, CH—N, 0.9).

EXAMPLE 34

9.7 g (0.1 mol) of 3-EAN and 21.9 g (0.3 mol) of diethylamine are refluxed for 4 h. Subsequent vacuum distillation yields 9.9 g (80% with respect to 3-EAN) of 3-diethylaminoacrylonitrile.

$^1$H-NMR ($CCl_4$): $\delta$=1.14 (t, I=7.0 Hz, $CH_{3tr}$, 5.8), 1.28 (t, I=7.0 Hz, $CH_{3cis}$, 0.2), 3.18 (q, I=7.0 Hz, $CH_{2tr}$), 3.38 (q, I=7.0 Hz, $CH_{2cis}$), 3.71 (d, $I_{tr}$=13.5 Hz, CH—CN, 1), 6.31 (d, $I_{cis}$=9.0 Hz, CH—N), 6.90 (d, $I_{tr}$=13.5 Hz, CH—N, 1).

EXAMPLE 35

14.6 g (0.15 mol) of 3-EAN and 24.8 g (0.25 mol) of cyclohexylamine are refluxed for 2 h with distillation of ethanol. After cooling off, the solid was suction filtered and washed with cold methanol. Yield 21.4 g (95.1% with respect to 3-EAN) of 3-cyclohexylaminoacrylonitrile.

$^1$H-NMR ($CDCl_3$): $\delta$=1–2 (m, $(CH_2)_5$, 10), 3.03 (m, 1), 3.75 (d, $I_{cis}$=8.4 Hz, CH—CN, 0.34), 3.93 (d, $I_{tr}$=13.8 Hz, CH—CN, 0.66), 4.88 (m, NH, 1) 6.66 (dd, $I_{NH}$=13.2 Hz, $I_{cis}$=8.4 Hz, CH—N), 6.95 (dd, $I_{NH}$=9.0 Hz, $I_{tr}$ 13.8 Hz, (CH—N).

EXAMPLE 36

19.4 g (0.2 mol) of 3-EAN and 21.3 g (0.3 mol) of pyrrolidine are refluxed for 2 hours. Subsequent vacuum distillation yields 23.6 g (96.3% with respect to 3-EAN) of 3-pyrrolidine acrylonitrile.

$^1$H-NMR (CDCl$_3$): δ=1.95 (m, (CH$_2$)$_2$, 4), 3.23 (m, (CH$_2$)$_2$, 4) 3.62 (d, $I_{tr}$=13.3 Hz, CH—CN, 1), 6.53 (d, $I_{cis}$=9.0 Hz, CH—N, 0.05), 7.14 (d, $I_{tr}$=13.3 Hz, CH—N, 0.95).

EXAMPLE 37

9.7 g (0.1 mol) of 3-EAN and 21.4 g (0.2 mol) of benzylamine are refluxed for 4 h with removal of ethanol by distillation. Subsequent vacuum distillation yields 11.4 g of 3-benzylaminoacrylonitrile (72% with respect to 3-EAN).

$^1$H-NMR (CDCl$_3$): δ=3.88 (d, $I_{tr}$=13.8 Hz, CH—CN, 1) 4.12 (d, $I_{NH}$=5.5 Hz, CH$_2$, 2), 5.3-6.2 (broad, NH) 6.7-7.6 (m, Ph, CH—N, g).

EXAMPLE 38

19.4 g (0.2 mol) of 3-EAN and 17 g (0.3 mol) of allyl amine are refluxed for 3 h. Subsequent vacuum distillation yields 20.3 g of 3-allylaminoacrylonitrile (94% with respect to 3-EAN).

$^1$H-NMR (CDCl$_3$): δ=3.52-3.98 (m, CH$_2$ $_{aliph.}$, CH—CN, 3), 5.09-5.32 (m, CH$_2$ $_{olef.}$), 5.66-5.86 (m, CH—C), 5.7 (broad, NH), 6.63 (dd, $I_{NH}$=12.7 Hz, $I_{cis}$=8.3 Hz, CH—N, 0.24), 7.05 (dd, $I_{NH}$=8.0 Hz, $I_{tr}$=13.8 Hz, CH—N, 0.76).

EXAMPLE 39

14.55 g (0.15 mol) of 3-EAN and 4.5 g (0.075 mol) of ethylene diamine are refluxed for 5 h with distillation of ethanol. After filtration and washing with cold methanol, 10.7 g of 3,3-N,N'-ethylenediamino-)bisacrylonitrile was obtained (88%).

$^1$H-NMR (acetone.d$_6$): δ=3.16-3.55 (m, CH$_2$, 4) 3.72 (d, $I_{cis}$=8.4 Hz, CH—CH, 0.34) 4.06 (d, $I_{tr}$=13.8 Hz, CH—CN, 1.66), 6.30 (s NH, 2), 6.78 (dd, $I_{NH}$=12.7 Hz, $I_{cis}$=8.4 Hz, CH—N), 7.12 (dd, $I_{NH}$=8.1 Hz, $I_{tr}$=13.8 Hz, CH—N).

EXAMPLE 40

9.7 g (0.1 mol) of 3-EAN and 12.8 g (0.15 mol) of piperidine are refluxed for 1.5 h. Subsequent vacuum distillation yields 12.5 g of 3-piperidinoacrylonitrile (91.7% with respect to 3-EAN.

$^1$H-NMR (CCl$_4$): δ=1.58 (m), (CH$_2$)$_3$, 6), 3.13 (m, (CH$_2$)$_2$, 4) 3.81 (d, $I_{tr}$=13.5 Hz, CH—CN), 6.37 (d, $I_{cis}$=9.0 Hz, CH—N, 0.3), 6.93 (d, $I_{tr}$=13.5 Hz, CH—N, 0.7).

EXAMPLE 41

16.7 g (0.15 mol) of 3-n-propoxyacrylonitrile and 17.0 g (0.2 mol) of piperidine are refluxed for 5 h. By distillation 17.1 g of 3-piperidinoacrylonitrile is obtained (84% with respect to n-propoxyacrylonitrile).

The spectrum is the same as the spectrum in Example 10.

EXAMPLE 42

48.5 g (0.5 mol) of 3-EAN and 21.8 g (0.25 mol) of morpholine are refluxed for 5 h. Subsequent vacuum distillation yields 31.3 g of 3-morpholinoacrylonitrile (90.7% with respect to morpholine).

$^1$H-NMR (CDCl$_3$): δ=3.11-3.75 (m, (CH$_2$)$_4$, CH—CN$_{cis}$), 3.94 (d, $I_{tr}$=13.7 Hz, CH—CN), 6.30 (d, $I_{cis}$=9.7 Hz, CH—N, 0.46), 6.90 (d, $I_{tr}$=13.7 Hz, CH—N, 0.54).

EXAMPLE 43

19.4 g (0.2 mol) of 3-EAN and 8.6 g (0.1 mol) of piperazine are refluxed for 2 h. The solid matter formed after cooling is suction filtered and washed with cold methane. 12.6 g (67%) of 3,3'-piperazinobisacrylonitrile was obtained.

$^1$H-NMR (DMSO-D$_6$): δ=3.24 (s, CH$_2$, 8) 4.17 (d, $I_{tr}$=13.5 Hz, CH—CN, 2) 7.20 (d, $I_{tr}$=13.5 Hz, CH—N, 2).

EXAMPLE 44

19.4 g (0.2 mol) of 3-EAN, 13.6 g (0.8 mol) of ammonia and 14.0 g (0.15 mol) of aniline are heated at 100° C. in an autoclave for 4 h. Then the mixture is dissolved in water and extracted with ether. The recrystallization of the concentrated extract from carbon tetrachloride yields 19.2 g of 3-anilinoacrylonitrile (88.9% with respect to aniline).

$^1$H-NMR (DMSO-d$_6$): δ=4.67 (d, $I_{tr}$=13.8 Hz, CH—CN, 1), 6.9-7.7 (m, Ph), 7.76 (dd, $I_{NH}$=12.8 Hz, $I_{tr}$=13.8 Hz, CH—N), 9.6 (d, broad, NH).

EXAMPLE 45

19.4 g (0.2 mol) of 3-EAN, 13.6 g (0.8 mol) of ammonia and 21.6 g (0.2 mol) of 2-aminopicoline are heated at 100° C. for 4 h in an autoclave, then dissolved in water and extracted with ether. Recrystallation of the concentrated extract with carbon tetrachloride yields 24.2 g (76%) of 3-(2-aminopicolino-)acrylonitrile.

$^1$H-NMR (DMSO d$_6$: δ=2.38 (s, CH$_3$, 3), 4.42 (d, $I_{cis}$=9.0 Hz, CH—CN, 0.96) 4.84 (d, $I_{tr}$=14.0 Hz, CH—CN, 0.04), 6.8-7.6 (m, CH$_{arom.}$), 8.00 (dd, $I_{NH}$=12.5 Hz, $I_{cis}$=9.0 Hz, CH—N), 9.96 (d, broad, I=12.5 Hz, NH, 1).

EXAMPLE 46

11.1 g (0.1 mol) of 2-methyl-3-ethoxyacrylonitrile and 15.2 g (0.2 mol) of 40% aqueous methylamine solution are kept for 15 h at 25° C. After extraction with ether, drying the ether phase and vacuum distillation, 8.15 g of 2-methyl-3-methylaminoacrylonitrile is obtained (84.9% with respect to 1-methyl-3-ethoxyacrylonitrile).

$^1$H-NMR (CDCl$_3$): δ=1.63 (d, I=1.2 Hz, CH$_3$—C$_{tr}$, 2.6), 1.73 (d, I=1.0 CH$_3$—C$_{cis}$, 0.4), 2.92 Cd, $I_{NH}$=4.8 Hz, CH$_3$—N, 3), 4.30 (s, broad, NH, 1), 6.44 (dq, $I_{NH}$=12.5 Hz, I=1.0 Hz, HC$_{cis}$), 6.63 (dq, $I_{NH}$=13.3 Hz, I 1.2 Hz, CH$_{tr}$).

EXAMPLE 47

2-Benzyl-3-ethoxyacrylonitrile is transposed with piperidine to 2-benzyl-3-piperidinoacrylonitrile in a manner similar to Example 40, with a good yield.

EXAMPLE 48

9.35 g (0.05 mol) of 2-benzyl-3-ethoxyacrylonitrile and 17.4 g (0.2 mol) of morpholine are refluxed for 20 h. Subsequent vacuum distillation yields 4.6 g of 2-benzyl-3-morpholinoacrylonitrile (81% with respect to the reacted 2-benzyl-3-ethoxyacrylonitrile (50%).

$^1$H-NMR (CDCl$_3$): δ=3.2 - 3.8 (m, CH$_2$, 8), 6.32 (s, CH, 1), 7.28 (s, Ph, 5).

The following Examples 49 to 66 relate to the preparation of 3-aminoacrylonitriles from metal salts of 3-hydroxyacrylonitrile.

EXAMPLE 49

12–35 g (0.126 mol) of sulfuric acid in 40 ml of ethanol is added slowly, with cooling, to a suspension of 32.5 g (0.25 mol) of sodium-3-hydroxyacrylonitrile (content 70%) in 200 ml of ammonia-saturated ethanol, and stirred for 5 h at 60° C. After removal of the solid by filtration, withdrawal of the solvent, extraction of the residue with acetic ester and withdrawal of the extractant, 13.1 g (77%) of 3-aminoacrylonitrile was obtained.

$^1$H-NMR (CDCl$_3$): δ=3.96 (d, I$_{cis}$=9.2 Hz, CH—CN), 4.25 (d, I$_{tr}$=13.8 Hz, CH—CN), 4.8–6.4 (broad, NH), 6.4–7.9 (m, CH—N).

EXAMPLE 50

32.5 g (0.25 mol) of sodium-3-hydroxyacrylonitrile (content 70%) and 20.3 g (0.3 mol) of methylamine hydrochloride are refluxed for 4 h in 100 ml of ethanol. After removal of the solid by filtration, and withdrawal of the solvent followed by vacuum distillation, 15.3 g of 3-methylaminoacrylonitrile is obtained (74.5%).

$^1$H-NMR (CDCl$_3$): δ=2.68 (d, I$_{NH}$ 5.0 Hz, CH$_{3tr}$, 2.8), 152.98 (d, I$_{NH}$=5.0 Hz, CH$_{3cis}$, 0.2), 3.67 (d, I$_{cis}$=8.5 Hz, CH—CN), 3.83 (d, I$_{tr}$=13.5 Hz, CH—CN), 5.71 (broad, NH, 1), 6.60 (dd, I$_{cis}$=12.0 Hz, I$_{cis}$=8.5 Hz, CH—CN), 7.12 (dd, I$_{NH}$=7.1 Hz, I$_{tr}$=13.5 Hz, CH—CN).

EXAMPLE 51

32.5 g (0.25 mol) of sodium-3-hydroxyacrylonitrile (content 70%) and 24.3 g (0.3 mol) of dimethylamine hydrochloride are heated at 50° C. for 40 h in 100 ml of ethanol. After working up as in Example 50, 16.8 g of 3-dimethylaminoacrylonitrile is obtained (70%).

$^1$H-NMR (CCl$_4$): δ=2.92 (s, CH$_{3tr}$, 5.8), 3.17 (s, CH$_{3cis}$, 0.2), 3,57 (d, I$_{cis}$=9.5 Hz, CH—CN), 3.75 (d, I$_{tr}$=13.5 Hz, CH—CN), 6.50 (d, I$_{cis}$=9.5 Hz, CH—N, 0.1), 17.15 (d, I$_{tr}$=13.5 Hz, CH—N, 0.9).

EXAMPLE 52 (Substance of Example 51)

30.3 g (0.25 mol) of sodium-3-hydroxyacrylonitrile (content 75%) and 24.3 g (0.3 mol) of dimethylamine hydrochloride are kept at 20° C. in 200 ml of water for 2 h. After extraction with chloroform and vacuum distillation, 20.1 g of 3-dimethylaminoacrylonitrile (83.7%) is obtained.

The $^1$H-NMR spectrum is the same as in Example 3.

EXAMPLE 53

32.5 g (0.25 mol) of sodium-3-hydroxyacrylonitrile (content 70%) is added to a solution of 25.6 g (0.35 mol) of diethylamine, 21.0 g (0.35 mol) of acetic acid and 150 ml of acetonitrile, and the mixture is stirred for 16 h at 25° C. After working up as in Example 50, 19.7 g of 3-diethylaminoacrylonitrile was obtained (63.6%).

$^1$H-NMR (CCl$_4$): δ=1.14 (t, I=7.0 Hz, CH$_{3tr}$, 5.8), 1.28 (t, I=7.0 Hz, CH$_{3cis}$, 0.2), 3,18 (q, I=7.0 Hz, CH$_{2tr}$), 3.38 (q, I=7.0 Hz, CH$_{2cis}$), 3.71 (d, I$_{tr}$=13.5 Hz, CH—CN), 6.31 (d, I$_{cis}$=9.0 Hz, CH—N), 6.90 (d, I$_{tr}$=13.5 Hz, CH—N, 1).

EXAMPLE 54

32.5 g (0.25 mol) of sodium-3-hydroxyacrylonitrile (content 70%) is added to a suspension of cyclohexylamine hydrochloride (composed of 29.8 g (0.3 mol) of cyclohexylamine and gaseous hydrochloric acid) in 150 ml of ethanol and the mixture is stirred for 24 h at 25° C. After removal of the solid by filtration, and withdrawal of the solvent followed by recrystallization from carbon tetrachloride, 32.1 g (85.6%) of 3-cyclohexylaminoacrylonitrile was obtained.

$^1$H-NMR (CDCl$_3$): δ=1–2 (m, (CH$_2$)$_5$, 10), 3.03 (m, 1), 3.75 (d, I$_{cis}$=8.2 Hz, CH—CN, 0.04), 3.93 (d, I$_{tr}$=13.8 Hz, CH—CN, 0.96), (m, NH, 1), 6.66 (dd, I$_{NH}$=13.2 Hz, I$_{cis}$=8.4 Hz, CH—CN), 6.95 (dd, I$_{NH}$=9.0 Hz, I$_{tr}$=13.8 Hz, CN—N).

EXAMPLE 55

32.5 g (0.25 mol) of sodium-3-hydroxyacrylonitrile (content 70%) is added to a mixture of 17.8 g (0.25 mol) of pyrrolidine, 12.3 g (0.125 mol) of sulfuric acid and 200 ml of ethanol, and the mixture is stirred at 50° C. for 7 h. After working up as in Example 50, 24.3 g of 3-pyrolidine acrylonitrile (79.6%) is obtained.

$^1$H-NMR (CDCl$_3$): =1.95 (m, (CH$_2$)$_2$ 4), 3.23 (m, (CH$_2$)$_2$, 4), 3.62 (d, I$_{tr}$=13.3 Hz, CH—CN, 1), 6.53 (d, I$_{cis}$=9.0 Hz, CH—N, 0.04), 7.14 (d, I$_{tr}$=13.3 Hz, CH—N, 0.96).

EXAMPLE 56

32.5 g (0.25 mol) of sodium-3-hydroxyacrylonitrile (content 70%) and 43.1 g (0.3 mol) of benzylamine hydrochloride are refluxed for 5 h in 150 ml of acetonitrile. After removal of the solid by filtration and withdrawal of the solvent, the product was dissolved in chloroform and washed with water. Subsequent vacuum distillation yielded 22.6 g of 3-benzylaminoacrylonitrile (57.1%).

$^1$H-NMR (CDCl$_3$): δ=3.88 (d, I$_{tr}$=13.8 Hz, CH—CN, 1), 4.12 (d, I$_{NH}$=5.5 Hz, CH$_2$, 2), 5.3–6.2 (broad, NH), 6.7–7.6 (m, Ph, CH—N, 6).

EXAMPLE 57

18 g (0.3 mol) of acetic acid is added to a suspension of 30.3 g (0.25 mol) of sodium-3-hydroxyacrylonitrile (content 75%) and 17 g (0.3 mol) of allylamine in 150 ml of methanol at 10° C., and the mixture is stirred at 25° C. After working up as in Example 50, 19.2 g of 3-allylaminoacrylonitrile (71.1%) was obtained.

$^1$H-NMR (CDCl$_3$): δ=3,523.98 (m, CH$_{2aliph.}$, CH—CN, 3), 5.09–5.32 (m, CH$_{2olef.}$), 5.66–5.86 (m, CH—C), 5.7 (broad, NH), 6.63 (dd, I$_{NH}$=12.7 Hz, I$_{cis}$=8.3 Hz, CH—N, 0.2), 7.05 (dd, I$_{NH}$=8.0 Hz, I$_{tr}$=13.8 Hz, CH—N, 0.8).

EXAMPLE 58

30.3 g (0.25 mol) of sodium-3-hydroxyacrylonitrile (content 75%) is added to a solution of 9 g (0.15 mol) of ethylene diamine in 150 ml of 2 N hydrochloric acid and stirred for 24 h at 25° C. The precipitated solid matter is filtered out and dried, and the mother liquor is extracted with chloroform. 12.1 g of 3,3-(N,N-ethylenediamino-)bis-acrylonitrile (59.8%) is obtained.

$^1$H-NMR (acetone, d$_6$): δ3.16–3.55 (m, CH$_2$, 4), 3.72 (d, I$_{cis}$=8.4 Hz, CH—CN, 0.3), 4.06 (d, I$_{tr}$=13.8 Hz, CH—CN, 1.66), 6.30 (s, NH, 2), 6.78 (dd, I$_{NH}$=12.7 Hz, I$_{cis}$ 8.4 Hz, CH—N), 7.12 (dd, I$_{NH}$=8.1 Hz, I$_{tr}$=13.8 Hz, CH—N).

EXAMPLE 59

30.3 g (0.25 mol) of sodium-3-hydroxyethylnitrile (content 75%) is added to a suspension of piperidine sulfate (prepared from 29.8 g (0.35 mol) of piperidine and 17.15 g (0.175 mol) of sulfuric acid) in 200 ml of methanol and stirred for 24 hours at 25° C. After working up as in Example 55, 28.2 g of 3-piperidinoacrylonitrile was obtained (82.9%).

$^1$H-NMR (CCl$_4$): $\delta$=1.58 (m, (CH$_2$)$_3$, 6), 3.13 (m, (CH$_2$)$_2$, 4), 3.81 (d, I$_{tr}$=13.5 Hz, CH—CN), 6.37 (d, I$_{cis}$=9.6 Hz, CH—N, 0.1), 6.93 (d, I$_{tr}$=13.5 Hz, CH—N, 0.9).

EXAMPLE 60 (Substance of Example 59)

30.3 g (0.25 mol) of sodium-3-hydroxyacrylonitrile (content 75%) is added to a suspension of 41.3 g (0.3 mol) of triethylamine hydrochloride and 21.3 g (0.25 mol) of piperidine in 200 ml of ethanol and maintained for 24 h at 25° C. After working up as in Example 56, 26.9 g of 3-piperidinoacrylonitrile is obtained (79.3%).

The $^1$H-NMR spectrum is the same as in Example 59.

EXAMPLE 61

30.3 g (0.25 mol) of sodium-3-hydroxyacrylonitrile (content 75%) is added to a solution of morpholine acetate (prepared from 26.1 g (0.3 mol) of morpholine and 18 g (0.3 mol) of acetic acid) in 200 ml of acetonitrile and is heated for 8 h at 65° C. After working up as in Example 55, 26.0 g (75.4%) of 3-morpholine acrylonitrile was obtained.

$^1$H-NMR (CDCl$_3$): $\delta$=3.11–3.75 (m, (CH$_2$)$_4$, CH—CN$_{cis}$), 3.94 (d, I$_{tr}$=13.7 Hz, CH—CN), 6.30 (d, I$_{cis}$=9.7 Hz, CH—N, 0.2), 6.90 (d, I$_{tr}$=13.7 Hz, CH—N, 0.8).

EXAMPLE 62

30.3 g (0.25 mol) of sodium-3-hydroxyacrylonitrile (content 75%) is added to a suspension of piperazine sulfate (prepared from 12.9 g (0.15 mol) of piperazine and 14.7 g (0.15 mol) of sulfuric acid) in 200 ml of acetonitrile and refluxed for 5 h. After removal of the solid by filtration and withdrawal of the solvent, the product was dissolved with chloroform and washed with water. After withdrawal of the chloroform and recrystallization of the residue from a mixture of acetic ester and carbon tetrachloride, 12.5 g of 3,3-piperazino-bisacrylonitrile was obtained (53.2%).

$^1$H-NMR (DMSO-D$_6$): $\delta$=3.24 (s, CH$_2$, 8), 4.17 (d, I$_{tr}$=13.5 Hz, CH—CN, 2), 7.20 (d, I$_{tr}$=13.5 Hz, CH—N, 2).

EXAMPLE 63

12.25 g (0.125 mol) of sulfuric acid in 30 ml of ethanol is added drop by drop, at 0° C., to a suspension of 32.5 g (0.25 mol) of sodium-3-hydroxyacrylonitrile and 32.6 g (0.35 mol) of aniline in 150 ml of ethanol, and the mixture is held at 25° C. for 5 h. After removal of the solid by filtration and withdrawal of the solvent, the product is dissolved with water, acidified with dilute sulfuric acid, and extracted with ether. After recrystallization of the concentrated ether extract from carbon tetrachloride, 24.3 g (67.6%) of 3-anilinoacrylonitrile is obtained.

$^1$H-NMR (DMSO. d$_6$): $\delta$=4.67 (d, I$_{tr}$=13.8 Hz, CH—CN, 1), 6.9–7.7, (m, Ph), 7.76 (dd, I$_{NH}$=12.8 Hz, I$_{tr}$=13.8 Hz, CH—N), 9.6, (d, broad, NH).

EXAMPLE 64

12.25 g (0.125 mol) of sulfuric acid in 30 ml of ethanol is added drop by drop at 0° C. to a suspension of 32.5 g (0.25 mol) of sodium-3-hydroxyacrylonitrile and 37.8 g (0.35 mol) of 2-aminopicoline in 150 ml of ethanol, and the mixture is held at 60° C. for 5 h. After working up as in Example 61, 24.9 g of 3-(2-aminopicolino-)acrylonitrile was obtained (62.7%).

$^1$H-NMR (DMSO.d$_6$): $\delta$=2.38 (s, CH$_3$, 3), 4.42 (d, I$_{cis}$=9.0 Hz, CH—CN, 0.98), 4.84 (d, I$_{tr}$=14.0 Hz, CH—CN, 0.02), 6.8 $\propto$ 7.6 (m, CH$_{arom.}$), 8.00 (dd, I$_{NH}$=12.5 Hz, I$_{cis}$=9.0 Hz, CH—N), 9.96 (d, broad, I=12.5 Hz, NH, 1).

EXAMPLE 65

7.35 g (0.1 mol) of sodium-2-methyl-3-hydroxyacrylonitrile (content 70%) and 10.1 g (0.15 mol) of methylamine hydrochloride are stirred at 20° C. in 100 ml of ethanol for 20 hours. After working up as in Example 50, 6.9 g of 2-methyl-3-methylaminoacrylonitrile is obtained (72.0%).

EXAMPLE 66

10.9 g (0.05 mol) of sodium-2-benzyl-3-hydroxyacrylonitrile (content 83%) and 12.5 g (0.15 mol) of dimethylamine hydrochloride are kept in 40 ml of water at 20° C. for 5 hours. After extraction with methylene chloride and vacuum distillation, 7.2 g of 2-benzyl-3-dimethylaminoacrylonitrile are obtained (89%).

$^1$H-NMR (CDCl$_3$): $\delta$=3.03 (s, CH$_3$, 6), 3.38 (s, CH$_2$, 2) 6.37 (s, CH, 1), 7.32 (s, Ph, 5).

EXAMPLE 67

27.6 g (0.35 mol) of acetyl chloride is stirred slowly into a suspension of 25.6 (0.2 mol) of sodium-3-hydroxyacrylonitrile (content 71%) in 150 ml of acetone, at 0° C. After 2 h of reaction at 20° C., the salt is separated and the mother liquor is concentrated. Subsequent distillation in vacuo yields 19.5 g of acetic acid-(2-cyanovinyl-)ester.

$^1$H-NMR (CDCl$_3$): $\delta$=2.25 (s, CH$_{3tr}$), 2.32 (s, CH$_{3cis}$), 3 H; 5.10 (d, I$_{cis}$=7 Hz, CH—CN), 5.43 (d, I$_{tr}$=13.4 Hz, CH—CN) 1 H; 7.93 (d, I$_{cis}$=7 Hz, CH—O, 0.55) 8.17 (d, I$_{tr}$=13.4 Hz, CH—O, 0.45).

EXAMPLE 68

Example 67 is repeated, but with ether as solvent instead of acetone.

Yield: 15.7 g acetic acid-(2-cyanovinyl) ester.

EXAMPLE 69

22.5 g (0.25 mol) of acetic acid anhydride is added slowly, at 0° C., to a suspension of 25.6 g (0.2 mol) of sodium-3-hydroxyacrylonitrile (content 71%) in 150 ml of benzene, and the mixture is stirred for 3 h at 25° C. After separation of the solid and withdrawal of the solvent, the product is vacuum-distilled.

Yield: 16.5 g of acetic acid-(2-cyanovinyl) ester (74.3%).

EXAMPLE 70

22.5 g (0.25 mol) of acetic acid anhydride is stirred slowly, at 0° C., into a suspension of 24.3 g (0.2 mol) of sodium-3-hydroxyacrylonitrile (content 75%) in 150 ml of acetonitrile, and the mixture is stirred for 2 h at 20° C. After separation of the solid and withdrawal of the solvent, the product is vacuum-distilled.

Yield: 21.6 g (97.3%) of acetic acid (2-cyanovinyl) ester.

EXAMPLE 71

35.1 g (0.25 mol) of benzoyl chloride is slowly added to a suspension of 25.6 g (0.2 mol) of sodium-3-hydroxyacrylonitrile (content 71%) in 150 ml of ether at 0° C., with stirring, and the mixture is stirred for 20 h at 25° C. The product is worked up as in Example 67.

Yield: 23.6 g of benzoic acid (2-cyanovinyl) ester (68%).

$^1$H-NMR (CDCl$_3$, $\delta$=5.11 (d, I$_{cis}$=6.8 Hz, CH—CN), 5.51 (d, I$_{tr}$=13 Hz, CH—CN), 7.2–8.6 (m, Ph and CH—O).

EXAMPLE 72

13.1 g (0.075 mol) of p-chlorobenzoyl chloride in 30 ml of ether is added drop by drop at −20° C. to a suspension of 9.1 g (0.075 mol) of sodium-3-hydroxyacrylonitrile (content 75%) in 75 ml of ether, and the mixture is held for 1 h at 0° C. After separation of the solid and withdrawal of the solvent, the product is recrystallized from acetic ester.

Yield: 8.9 g of p-chlorobenzoic acid-(2-cyanovinyl) ester (57%).

$^1$H-NMR (CDCl$_3$): $\delta$=5.18 (d, I$_{cis}$=6.8 Hz, CH—CN), 5.58 (d, I$_{tr}$=13.5 Hz, CH—CN) 1 H; 7.3–8.7 (m, Ph and CH—O, 5).

EXAMPLE 73

19.4 g (0.125 mol) of succinic acid dichloride is added slowly, with stirring, at 10° C., to a suspension of 25.6 g (0.2 mol) of sodium-3-hydroxyacrylonitrile (content 71%) in 200 ml of benzene, and the mixture is stirred for 2 hours at 20° C. The residue obtained after separation of the solid and withdrawal of the solvent is washed with carbon tetrachloride and suction filtered. 4.4 grams of succinic acid-bis-(2-cyanovinyl) ester remains as filtrate (20%).

$^1$H-NMR (DMSO-d$_6$) $\delta$=2.96 (s, CH$_2$, 4); 5.47 (d, I$_{cis}$=7 Hz, CH—CN), 5.82 (d, I$_{tr}$=13.5 Hz, CH—CN) 2 H; 8.07 (d, I$_{cis}$=7 Hz, CH—O 0.08), 8.30 (d, I$_{tr}$=13.5 Hz, CH—O, 1.2).

EXAMPLE 74

20.3 g (0.1 mol) of isophthalic acid dichloride in 50 ml of ether is added drop by drop at −10° C. to a suspension of 24.2 g (0.2 mol) of sodium-3-hydroxyacrylonitrile (content 75%) in 200 ml of ether, and the mixture is held for 2 hours at 0° C. After separation of the solid and withdrawal of the solvent, the product is recrystallized from acetic ester. Yield: 11.8 g (44%) of isophthalic acid-bis-(2-cyanovinyl) ester.

$^1$H-NMR (DMSO-d$_6$): $\delta$=5.74 (d, I$_{cis}$=6.8 Hz, CH—CN), 6.15 (d, I$_{tr}$=13 Hz, CH—CN) 2 H; 7.5–8.7 (m, Ph and CH—O) 6 H.

EXAMPLE 75

24.8 g (0.243 mol) of acetic anhydride is stirred slowly at a temperature below 10° C. into a suspension of 28 g (0.187 mol) of sodium-2-methyl-3-hydroxyacrylonitrile (content 70%) in 125 ml of toluene, and the mixture is stirred for 24 h at 20° C. The product is worked up as in Example 67. Yield: 18.7 g (80%) of acetic acid-(2-methyl-2-cyanovinyl) ester.

$^1$H-NMR (CDCl$_3$): $\delta$=1.92, 2.00 (s, CH$_3$—C—CN$_{cis,}$ $_{tr}$,3), 2.32 (s, CH$_3$—C=O, 3, 7.6–8.1 (m, CH, 1).

EXAMPLE 76

2.65 g (0.026 mol) of acetic anhydride is added slowly, drop by drop, with stirring, at 0° C., to a suspension of 4.5 g (0.02 mol) of sodium-2-benzyl-3-hydroxyacrylonitrile (content 83%) in 20 ml of acetonitrile and the mixture is stirred for 3 h at 20° C. After separation of the solid and withdrawal of the solvent, the product is vacuum-destilled. Yield: 3,44 g (93%) of acetic acid-(2-benzyl-2-cyanovinyl) ester.

$^1$H-NMR (CDCl$_3$):=2,09 (s, CH$_3$ cis), 2,12 (s, CH$_{3tr}$), 3 H; 3,43 (d, J=1,0 Hz, CH$_{2\,cis}$, 0,76), 3,60 (d, J=1,0 Hz, CH$_{2tr}$, 1,24); 7,31 (s, Ph, 5); 7,81 (t, J=1,0 Hz, Ch$_{cis}$), 7,92 (t, J=1,0 Hz, CH$_{tr}$) 1 H.

What is claimed is:

1. A process for the preparation of a beta-alkoxyacrylonitrile of the formula $$R'O—CH=CR—CN \qquad (C)$$

wherein R represents H, straight-chain or branched or cyclic alkyl moieties of 1 to 20 C atoms, straight-chain or branched moieties—(CH$^2$)$_n$—CN, —(CH$_2$)$_n$—OR" or —(CH$_2$)$_n$—CH(OR")$_2$ with n=0 to 5 and R"=alkyl moieties with 1-12 C atoms, or —(CH$_2$)$_{n+1}$—Cyc, with Cyc=isocyclic or heterocyclic, mononuclear or polynuclear aromatic or cycloaliphatic ring systems, which in some cases bear substituents on the rings, and n=0 to 5, and wherein R' represents straight-chain or branched alkyl or alkenyl moieties with 1 to 12 C atoms, isocyclic or heterocyclic, mononuclear or polynuclear aromatic or cycloaliphatic ring systems, which in some cases bear substituents, or —(CH$_2$)$_p$—Cyc with Cyc in the above meaning, the moieties —(CH$_2$)$_p$—OR''' or —(CH$_2$—CH$_2$—O)$_q$—R''' with p=1 to 5 and q=1 to 4 and R'''=straight-chain or branched alkyl moieties with 1 to 12 C atoms, which comprises contacting a compound of the formula $$(1/\alpha Me)\,O—CH=CR—CN \qquad (A)$$

wherein R has the above-named meaning and Me is an alkali metal with $\alpha$=1 or an alkaline earth metal with $\alpha$=2, at an elevated temperature with a halogen compound of the formula R'-Hal (B), wherein R' has the above-given meaning and Hal represents chlorine, bromine or iodine, in the presence of a basically reacting compound of the alkali metal or alkaline earth metal, as stabilizer.

2. A process according to claim 1, wherein a quaternary ammonium salt or a crown ether is added as catalyst.

3. A process according to claim 2, wherein a quaternary ammonium salt is employed and said salt is of the general formula E is used as catalyst, $$\begin{array}{c} R^2 \\ | \\ R^1—N^\oplus—R^3 \quad X^\ominus \\ | \\ R^4 \end{array} \qquad (D)$$

wherein R$^1$, R$^2$, R$^3$ and R$^4$ represent identical or different cycloalkyl, aryl, alkaryl, aralkyl or alkyl moieties, which can be linear or branched, having 1 to 20 C atoms, and X represents a monovalent anion.

4. A process according to claim 2, wherein a crown ether is used as catalyst.

5. A process according to claim 2, wherein the quaternary ammonium salt or crown ether is used in an amount of $10^{-3}$ to $10^{-1}$ mole, with respect to the compound A.

6. A process according to claim 2, wherein as additional catalyst, an iodine compound in the form of an iodide or of a compound capable of forming iodine ions is present in the reaction mixture.

7. A process according to claim 6, wherein the iodine compound is present in the ratio of $10^{-3}$ to $10^{-1}$ mole per mole of compound of General Formula A.

8. A process according to claim 1, wherein an aprotic medium is used as solvent.

9. A process according to claim 1, wherein the reaction temperature is between 60° to 220° C.

* * * * *